United States Patent [19]

Ayer

[11] 4,145,535

[45] Mar. 20, 1979

[54] PYRAN ANALOGS OF TRANS-4,5-DIDEHYDRO-PGI COMPOUNDS

[75] Inventor: Donald E. Ayer, Kalamazoo, Mich.

[73] Assignee: The Upjohn Company, Kalamazoo, Mich.

[21] Appl. No.: 893,772

[22] Filed: Apr. 5, 1978

Related U.S. Application Data

[63] Continuation-in-part of Ser. No. 821,542, Aug. 3, 1977.

[51] Int. Cl.$^2$ ............................................. C07D 311/02
[52] U.S. Cl. ................................... 542/426; 542/418; 542/421; 542/429; 260/345.2
[58] Field of Search ..................... 260/345.2; 542/418, 542/421, 426, 429

[56] References Cited

PUBLICATIONS

Johnson et al., J.A.C.S. 99:12, Jun. 8, 1977, pp. 4182–4184.

Primary Examiner—Natalie Trousof
Assistant Examiner—Bernard Dentz
Attorney, Agent, or Firm—Robert A. Armitage

[57] ABSTRACT

The present invention provides pyran analogs of trans-4,5-didehydro-PGI compounds, which are useful pharmacological agents. The compounds of the present invention exhibit prostacyclin-like pharmacological properties.

55 Claims, No Drawings

PYRAN ANALOGS OF TRANS-4,5-DIDEHYDRO-PGI COMPOUNDS

CROSS REFERENCE TO RELATED APPLICATIONS

This application is a continuation-in-part of Ser. No. 821,542, filed Aug. 3, 1977, now pending issuance as a U.S. patent.

The present invention relates to pyran analogs of trans-4,5-didehydro-$PGI_1$ compounds, the essential material constituting a disclosure thereof being hereby incorporated from U.S. Pat. No. 4,109,082, issued Aug. 22, 1978.

I claim:

1. A prostacyclin analog of the formula

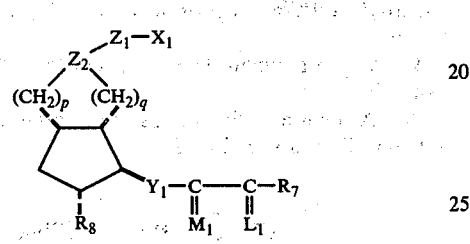

wherein $Z_2$ is

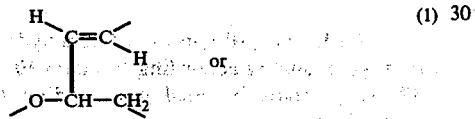 (1)

or

 (2)

wherein one of p and q is the integer one and the other is the integer zero;

wherein $Z_1$ is
(1) —$(CH_2)_g$—$CH_2$—$CH_2$—, or
(2) —$(CH_2)_g$—$CH_2$—$CF_2$—,
wherein g is the integer zero, one, or 2;
wherein $R_8$ is hydrogen, hydroxy, or hydroxymethyl;
wherein $Y_1$ is
(1) trans—CH=CH—,
(2) cis—CH=CH—, or
(3) —$CH_2CH_2$—,
wherein $M_1$ is

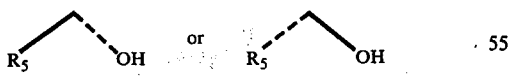

wherein $R_5$ is hydrogen or alkyl with one to 4 carbon atoms, inclusive,
wherein $L_1$ is

or a mixture of

and

, wherein $R_3$ and $R_4$ are hydrogen, methyl, or fluoro, being the same or different, with the proviso that one of $R_3$ and $R_4$ is fluoro only when the other is hydrogen or fluoro;

wherein $X_1$ is
(1) —$COOR_1$ wherein $R_1$ is hydrogen; alkyl of one to 12 carbon atoms, inclusive; cycloalkyl of 3 to 10 carbon atoms, inclusive; aralkyl of 7 to 12 carbon atoms, inclusive; phenyl; phenyl substituted with one, two or three chloro or alkyl of one to 3 carbon atoms; phenyl substituted in the para position by

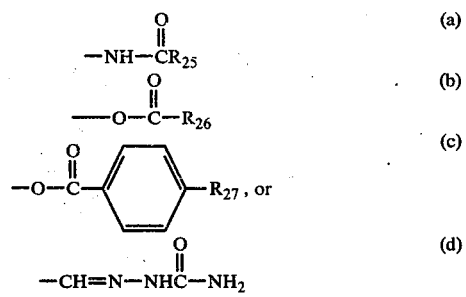

wherein $R_{25}$ is methyl, phenyl, acetamidophenyl, benzamidophenyl, or —$NH_2$; $R_{26}$ is methyl, phenyl, —$NH_2$, or methoxy; and $R_{27}$ is hydrogen or acetamido; inclusive, phenacyl, i.e.,

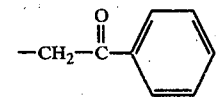;

phenacyl substituted in the para position by chloro, bromo, phenyl, or benzamido; or a pharmacologically acceptable cation;
(2) —$CH_2OH$;
(3) —$CH_2NL_2L_3$ wherein $L_2$ and $L_3$ are hydrogen or alkyl of one to 4 carbon atoms, inclusive; or
(4) —$COL_4$, wherein $L_4$ is
(a) amino of the formula —$NR_{21}R_{22}$, wherein $R_{21}$ and $R_{22}$ are hydrogen; alkyl of one to 12 carbon atoms, inclusive; cycloalkyl of 3 to 10 carbon atoms, inclusive; aralkyl of 7 to 12 carbon atoms, inclusive; phenyl; phenyl substituted with one, 2, or 3 chloro, alkyl of one to 3 carbon atoms, inclusive; hydroxy, carboxy, alkoxycarbonyl of one to 4 carbon atoms, inclusive, or nitro; carboxyalkyl of one to 4 carbon atoms, inclusive; carbamoylalkyl of one to 4 carbon atoms, inclusive; cyanoalkyl of one to 4 carbon atoms, inclusive; acetylalkyl of one to 4 carbon atoms, inclusive; benzoylalkyl of one to 4 carbon atoms, inclusive; benzoylalkyl substituted by one, 2, or 3 chloro, alkyl of one to 3 carbon atoms, inclusive; hydroxy, alkoxy of one to 3 carbon atoms, inclusive; carboxy, alkoxycarbonyl of one to 4 carbon atoms, inclusive; or nitro; pyridyl; pyridyl substituted by one, 2, or 3 chloro, alkyl of one to 3 carbon atoms, inclusive; or alkoxy of one to 3 carbon atoms, inclusive; pyridylalkyl of one to 4 carbon atoms, inclusive; pyridylalkyl substituted by one, 2, or 3 chloro, alkyl of one to 3 carbon atoms inclusive; hydroxy, alkoxy of one to 3 carbon atoms, inclusive; hydroxyalkyl of one to 4 carbon atoms, inclusive; dihydroxyalkyl of one to 4 carbon atoms, and trihydroxyalkyl of one to 4 carbon atoms; with the further proviso that not more than one of $R_{21}$ and $R_{22}$ is other than hydrogen or alkyl;

(b) cycloamino selected from the group consisting of

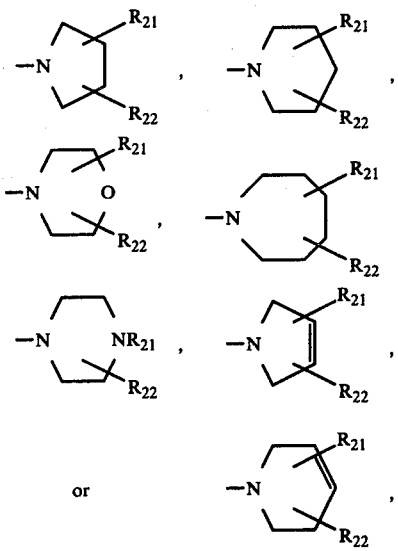

wherein $R_{21}$ and $R_{22}$ are as defined above;
(c) carbonylamino of the formula $-NR_{23}COR_{21}$, wherein $R_{23}$ is hydrogen or alkyl of one to 4 carbon atoms and $R_{21}$ is as defined above;
(d) sulphonylamino of the formula $-NR_{23}SO_2R_{21}$, wherein $R_{21}$ and $R_{23}$ are as defined above; or
(e) hydrazino of the formula $-NR_{23}R_{24}$, wherein $R_{23}$ is as defined above and $R_{24}$ is amino of the formula $-NR_{21}R_{22}$, as defined above, or cycloamino, as defined above;

wherein $R_7$ is $-(CH_2)_m-CH_3$, (1)

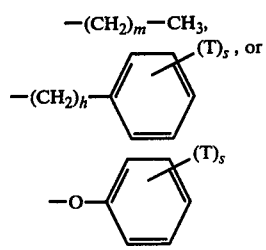

wherein m is the integer one to 5, inclusive, h is the integer zero to 3, inclusive; s is the integer zero, one, 2, or 3, and T is chloro, fluoro, trifluoromethyl, alkyl of one to 3 carbon atoms, inclusive, or alkoxy of one to 3 carbon atoms, inclusive, with the proviso that not more than two T's are other than alkyl; and the pharmacologically acceptable acid addition salts thereof when $X_1$ is $-CH_2NL_2L_3$.

2. A prostacyclin analog according to claim 1, wherein $R_8$ is hydroxymethyl.

3. 11-Deoxy-11α-hydroxymethyl-7a-homo-trans-4,5-didehydro-6α-$PGI_1$, a prostacyclin analog according to claim 2.

4. A prostacyclin analog according to claim 1, wherein $R_8$ is hydrogen.

5. 11-Deoxy-7a-homo-trans-4,5-didehydro-6α-$PGI_1$, a prostacyclin analog according to claim 4.

6. A prostacyclin analog according to claim 1, wherein $R_8$ is hydroxy.

7. A prostacyclin analog according to claim 6, wherein p is one.

8. (6R)-trans-4,5-Didehydro-9-deoxy-6,9α-epoxymethylene-$PGF_1$, a prostacyclin analog according to claim 7.

9. A prostacyclin analog according to claim 6, wherein q is one.

10. A prostacyclin analog according to claim 6, wherein $Z_2$ is a mixture of $$\begin{array}{c} H \\ \diagdown \\ C=C \\ | \\ O-CH-CH_2 \end{array} \diagup^H \quad \text{and} \quad \begin{array}{c} H \\ \diagdown \\ C=C \\ | \\ O-CH-CH_2 \end{array} \diagup^H$$

11. 7a-Homo-(6RS)-trans-4,5-didehydro-$PGI_1$, a prostacyclin analog according to claim 10.

12. A prostacyclin analog according to claim 6, wherein $Z_2$ is $$\begin{array}{c} H \\ \diagdown \\ C=C \\ | \\ O-CH-CH_2 \end{array} \diagup^H$$

13. 7a-Homo-trans-4,5-didehydro-6α-$PGI_1$, a prostacyclin analog according to claim 12.

14. 7a-Homo-15-methyl-trans-4,5-didehydro-6α-$PGI_1$, a prostacyclin analog according to claim 12.

15. 7a-Homo-16,16-dimethyl-trans-4,5-didehydro-6α-$PGI_1$, a prostacyclin analog according to claim 12.

16. 7a-Homo-2,2-difluoro-15-methyl-trans-4,5-didehydro-6α-$PGI_1$, a prostacyclin analog according to claim 12.

17. A prostacyclin analog according to claim 6, wherein $Z_2$ is $$\begin{array}{c} H \\ \diagdown \\ C=C \\ | \\ O-CH-CH_2 \end{array} \diagup^H$$

18. A prostacyclin analog according to claim 17, wherein $Y_1$ is cis—CH=CH—.

19. 7a-Homo-cis-13-trans-4,5-didehydro-6β-$PGI_1$, a prostacyclin analog according to claim 18.

20. A prostacyclin analog according to claim 17, wherein $Y_1$ is $-CH_2CH_2-$.

21. 7a-Homo-13,14-dihydro-trans-4,5-didehydro-6β-$PGI_1$, a prostacyclin analog according to claim 20.

22. 7a-Homo-13,14-dihydro-15-methyl-trans-4,5-didehydro-6β-PGI₁, a prostacyclin analog according to claim 20.

23. 7a-Homo-13,14-dihydro-16,16-dimethyl-trans-4,5-didehydro-6β-PGI₁, a prostacyclin analog according to claim 20.

24. 7a-Homo-13,14-dihydro-2,2-difluoro-15-methyl-trans-4,5-didehydro-6β-PGI₁, a prostacyclin analog according to claim 20.

25. 7a-Homo-13,14-dihydro-2,2,16,16-tetrafluoro-trans-4,5-didehydro-6β-PGI₁, a prostacyclin analog according to claim 20.

26. A prostacyclin analog according to claim 17, wherein $Y_1$ is trans—CH=CH—.

27. A prostacyclin analog according to claim 26, wherein $Z_1$ is —(CH₂)$_g$—CH₂—CF₂—.

28. 7a-Homo-2,2-difluoro-15-methyl-trans-4,5-didehydro-6β-PGI₁, a prostacyclin analog according to claim 27.

29. 7a-Homo-2,2-difluoro-16,16-dimethyl-trans-4,5-didehydro-6β-PGI₁, a prostacyclin analog according to claim 27.

30. 7a-Homo-2,2,16,16-tetrafluoro-trans-4,5-didehydro-6β-PGI₁, a prostacyclin analog according to claim 27.

31. A prostacyclin analog according to claim 26, wherein $Z_1$ is —(CH₂)$_g$—CH₂—CH₂—.

32. A prostacyclin analog according to claim 31, wherein g is zero.

33. A prostacyclin analog according to claim 32, wherein $R_7$ is

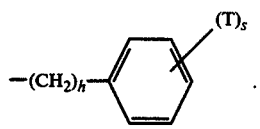

34. 7a-Homo-17-phenyl-18,19,20-trinor-trans-4,5-didehydro-6β-PGI₁, a prostacyclin analog according to claim 33.

35. A prostacyclin analog according to claim 32, wherein $R_7$ is

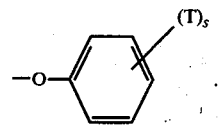

36. 7a-Homo-16-phenoxy-17,18,19,20-tetranor-trans-4,5-didehydro-6β-PGI₁, a prostacyclin analog according to claim 35.

37. A prostacyclin analog according to claim 32, wherein $R_7$ is —(CH₂)$_m$—CH₃—.

38. A prostacyclin analog according to claim 37, wherein m is 3.

39. A prostacyclin analog according to claim 38, wherein $X_1$ is —COL₄.

40. 7a-Homo-trans-4,5-didehydro-6β-PGI₁, amide, a prostacyclin analog according to claim 39.

41. A prostacyclin analog according to claim 39, wherein $X_1$ is —CH₂OH.

42. 7a-Homo-2-decarboxy-2-hydroxymethyl-trans-4,5-didehydro-6β-PGI₁, a prostacyclin analog according to claim 41.

43. A prostacyclin analog according to claim 38, wherein $X_1$ is —COOR₁.

44. A prostacyclin analog according to claim 43, wherein $R_5$ is methyl.

45. 7a-Homo-15-methyl-trans-4,5-didehydro-6β-PGI₁, a prostacyclin analog according to claim 44.

46. A prostacyclin analog according to claim 43, wherein $R_5$ is hydrogen.

47. A prostacyclin analog according to claim 46, wherein at least one of $R_3$ and $R_4$ is fluoro.

48. 7a-Homo-16,16-difluoro-trans-4,5-didehydro-6β-PGI₁, a prostacyclin analog according to claim 47.

49. A prostacyclin analog according to claim 46, wherein at least one of $R_3$ and $R_4$ is methyl.

50. 7a-Homo-16,16-dimethyl-trans-4,5-didehydro-6β-PGI₁, a prostacyclin analog according to claim 49.

51. A prostacyclin analog according to claim 46, wherein $R_3$ and $R_4$ are both hydrogen.

52. 7a-Homo-trans-4,5-didehydro-6β-PGI₁, methyl ester, a prostacyclin analog according to claim 51.

53. 7a-Homo-trans-4,5-didehydro-6β-PGI₁, tris(hydroxymethyl)amino methane salt, a prostacyclin analog according to claim 51.

54. 7a-Homo-trans-4,5-didehydro-6β-PGI₁, adamantanamine salt, a prostacyclin analog according to claim 51.

55. 7a-Homo-trans-4,5-didehydro-6β-PGI₁, a prostacyclin analog according to claim 51.

* * * * *

UNITED STATES PATENT OFFICE
CERTIFICATE OF CORRECTION

Patent No. 4,145,535                     Dated March 20, 1979

Inventor(s) Donald E. Ayer

It is certified that error appears in the above-identified patent and that said Letters Patent are hereby corrected as shown below:

IN THE TITLE: "PGI COMPOUNDS" should read -- $PGI_1$ COMPOUNDS --

In the Abstract, line 2, "PGI compounds" should read -- $PGI_1$ compounds --

Signed and Sealed this

Thirty-first Day of July 1979

[SEAL]

Attest:

LUTRELLE F. PARKER
Attesting Officer    Acting Commissioner of Patents and Trademarks